(12) United States Patent
Foos et al.

(10) Patent No.: US 9,427,203 B2
(45) Date of Patent: *Aug. 30, 2016

(54) METHOD AND SYSTEM FOR QUANTITATIVE IMAGING

(71) Applicant: Carestream Health, Inc., Rochester, NY (US)

(72) Inventors: David H. Foos, Webster, NY (US); Samuel Richard, Rochester, NY (US); Xiaohui Wang, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/930,995

(22) Filed: Nov. 3, 2015

(65) Prior Publication Data

US 2016/0051216 A1    Feb. 25, 2016

Related U.S. Application Data

(63) Continuation of application No. 14/050,920, filed on Oct. 10, 2013, now Pat. No. 9,204,853.

(60) Provisional application No. 61/712,480, filed on Oct. 11, 2012.

(51) Int. Cl.
| | |
|---|---|
| G01N 23/04 | (2006.01) |
| A61B 6/00 | (2006.01) |
| A61B 6/06 | (2006.01) |
| A61B 6/02 | (2006.01) |

(52) U.S. Cl.
CPC ............... *A61B 6/5217* (2013.01); *A61B 6/06* (2013.01); *A61B 6/4007* (2013.01); *A61B 6/4405* (2013.01); *A61B 6/4429* (2013.01); *A61B 6/461* (2013.01); *A61B 6/50* (2013.01); *A61B 6/563* (2013.01); *A61B 6/022* (2013.01)

(58) Field of Classification Search
CPC ........ A61B 6/05; A61B 6/06; A61B 6/4405; A61B 6/5217; A61B 6/563; A61B 6/022
See application file for complete search history.

(56) References Cited

U.S. PATENT DOCUMENTS

| | | | |
|---|---|---|---|
| 6,118,842 A | 9/2000 | Arai et al. | |
| 7,934,853 B2 | 5/2011 | Coombs et al. | |
| 8,050,743 B2 | 11/2011 | Daghighian | |
| 8,150,110 B2 | 4/2012 | Huo et al. | |
| 9,204,853 B2 * | 12/2015 | Foos | A61B 6/50 |
| 2003/0095692 A1 * | 5/2003 | Mundy | A61B 6/00 382/128 |
| 2011/0110496 A1 | 5/2011 | Foos et al. | |
| 2011/0200175 A1 | 8/2011 | Gregerson et al. | |

* cited by examiner

*Primary Examiner* — Courtney Thomas

(57) ABSTRACT

A system and method for digital x-ray imaging. The method includes emitting a first and second collimated x-ray beam from an x-ray source disposed in a first and second position, respectively. The first and second collimated x-ray beam is directed onto an identified region of interest (ROI) wherein a first and second ROI image is captured, respectively, when the x-ray source is disposed in the first and second position, respectively. The first and second ROI images are processed to extract features from each of the first and second ROI images. The extracted features are analyzed, and an indicator of a disease is generated responsive to the extracted features. The indicator can be stored, displayed, or transmitted. The first and second x-ray sources can be the same or different x-ray sources.

14 Claims, 13 Drawing Sheets

METHOD AND SYSTEM FOR QUANTITATIVE IMAGING

CROSS REFERENCE TO RELATED APPLICATIONS

This application is a Continuation of U.S. Ser. No. 14/050,920 filed on Oct. 10, 2013 titled "METHOD AND SYSTEM FOR QUANTITATIVE IMAGING" in the names of Foos et al, which granted on Dec. 8, 2015 as U.S. Pat. No. 9,204,853, which claims the benefit of U.S. Provisional application U.S. Ser. No. 61/712,480, provisionally filed on Oct. 11, 2012 entitled "METHOD AND SYSTEM FOR QUANTITATIVE IMAGING OF INTENSIVE CARE UNIT PATIENTS", in the names of Foos et al, all of which are incorporated herein by reference in their entirety.

FIELD OF THE INVENTION

The invention relates generally to the field of medical imaging.

BACKGROUND

The chest x-ray is a useful diagnostic tool that assists in detecting a number of patient conditions and for imaging a range of skeletal and organ structures. Radiographic images of the chest can be useful for detection of lung nodules and other features that indicate lung cancer and other pathologic structures. In clinical applications such as in the Intensive Care Unit (ICU), the chest x-ray can have particular value for indicating pneumothorax and other clinical conditions.

SUMMARY

Certain embodiments described herein address the need for quantitative analysis of Intensive Care Unit (ICU) patient images.

Another aspect of the present invention is to distinguish among the possible causes of regions of lung opacity.

Any aspects provided are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a digital x-ray imaging system, comprising: an x-ray source adapted to emit an x-ray beam; a collimator to collimate the x-ray beam to an identified region of interest; a positioning system to translate or rotate the x-ray source from a first position to a second position, wherein the second position is different than the first position; a digital x-ray detector adapted to capture a first image of the region of interest when the x-ray source is in the first position, and capture a second image of the region of interest when the x-ray source is in the second position; a processing engine to extract features from each of the region of interest of the first and second captured images; and an analyzer analyzing the extracted features and generating an indicator of a disease responsive to the extracted features.

According to another aspect of the invention, there is provided a digital x-ray imaging system, comprising: an x-ray source adapted to emit an x-ray beam; a collimator to collimate the x-ray beam to an identified region of interest; a first x-ray source in a first position; a second x-ray source in a second position, wherein the second position is different than the first position; a digital x-ray detector adapted to capture a first image of the region of interest using the first x-ray source disposed in the first position, and capture a second image of the region of interest using the second x-ray source disposed in the second position; a processing engine to extract features from each of the region of interest of the first and second captured images; and an analyzer analyzing the extracted features and generating an indicator of a disease responsive to the extracted features.

According to a further aspect of the invention, there is provided a method for digital x-ray imaging, comprising: emitting a first collimated x-ray beam from an x-ray source disposed in a first position; directing the first collimated x-ray beam onto an identified region of interest (ROI) and capturing a first ROI image; emitting a second collimated x-ray beam from the x-ray source disposed in a second position, wherein the second position is different than the first position; directing the second collimated x-ray beam onto the identified region of interest and capturing a second ROI image; processing the first and second ROI images to extract features from each of the first and second ROI images; analyzing the extracted features; generating at least one indicator of a disease responsive to the analyzed extracted features; and storing, displaying, or transmitting the at least one indicator.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF EXEMPLARY EMBODIMENTS

Figure 1:
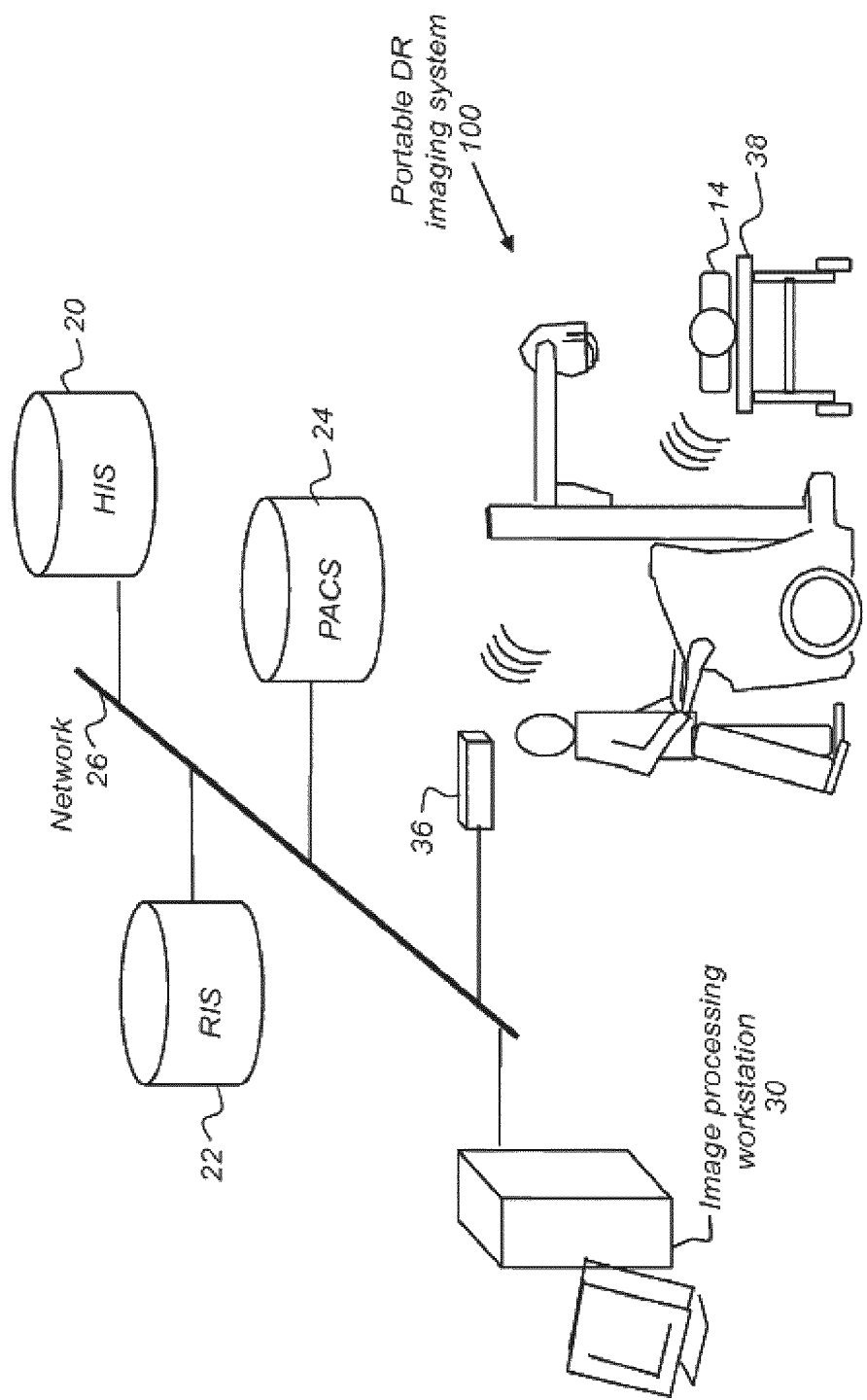
FIG. 1 shows an x-ray imaging system according to an embodiment of the present invention.

The following is a detailed description of the embodiments of the invention, reference being made to the drawings in which the same reference numerals identify the same elements of structure in each of the several figures.

This disclosure describes a method and system that is suitable for quantitative analysis of Intensive Care Unit (ICU) patient images. In particular, the method and system is suitable for distinguishing among the possible causes of regions of lung opacity.

Opacity refers to an area that preferentially attenuates the x-ray beam and therefore appears more opaque than the surrounding area. Opacities in chest x-ray refer to white smudges on the lung areas. Normal lungs appear dark on x-ray films because they are filled with air. Any material denser than air would appear as an opacity. This could represent a collection of thickened lung tissue secondary to under inflation (not breathing deep) or pneumonia, or several blood vessels and ribs overlying one another. For example, "suspicious faint opacity in upper lobes" may suggest a diagnosis of pulmonary tuberculosis or a lung mass, depending on the characteristics of the opacity.

Mobile/portable x-ray radiographic imaging systems that can be wheeled up to a patient's bedside, such as in an Intensive Care Unit (ICU) facility, can be employed for imaging patients to evaluate patient health and determine appropriate/best treatment.

However, abnormal findings on portable chest x-ray images of ICU patients are frequently nonspecific. Nonspecific findings are typically visualized as regions of opacity in the lung, but without any clear indication of whether the pathology is in the airways (e.g., lung collapse), airspaces (consolidation) or within the pleura (effusions). Establishing the correct diagnosis is desirable so as to initiate appropriate patient management.

Differentiating among types of pleural effusions is another common task assisted by imaging in the ICU and can be challenging and critical to patient care. Various types of fluids can cause plural effusions [e.g., blood (hemothorax), pus (pyothorax or empyema), and water/serous fluid (hydrothorax)]. Furthermore, each cause requires a different course of action.

Therefore, improved ability to identify the cause is beneficial. That is, knowing the cause with greater probability would be expected to enhance patient care.

In situations where mobile/portable radiographic imaging is found insufficient, Computed Tomography (CT) might be prescribed as it provides a full 3D image. However, acquiring a CT image can be disruptive to the patient who is in critical care. For example, obtaining a CT in such situations requires transporting an unstable patient out of the ICU which increases risk to the patient's already critical condition. An alternative to CT could be a bedside x-ray imaging system that is capable of providing quantitative information that will improve the specificity of findings that are identified on standard portable chest radiography. Such a system would be beneficial because it would reduce the need to transport unstable ICU patients for CT exams.

This disclosure describes a method and system that is suitable for quantitative analysis, particularly for ICU patient images. In particular, the method and system is suitable for distinguishing among the possible causes of regions of lung opacity.

The system employs an x-ray imaging system for capturing a plurality of x-ray images, wherein each image includes an identified region of interest (ROI). The system includes: a digital x-ray detector adapted for image acquisition; an x-ray generator/source adapted for x-ray exposures; a collimator adapted to focus/cone-down to a region of interest; and a positioning system that allows images of the identified region of interest (ROI) to be captured with different geometries, x-ray focus spot sizes, or other acquisition system parametric variations that can produce images of the ROI having different characteristic properties.

In at least one arrangement, the digital x-ray detector includes a digital x-ray detector adapted for rapid sequential image acquisition, and high frame rate readout for an identified region of interest, for example, an identified central region of the detector.

In another embodiment, the system is a digital mobile/portable x-ray imaging system.

A processing engine is employed to extract features from each of the ROI of the images. The extracted features are then analyzed using an analyzer, such as a statistical predictive model or trained neural network. An output is generated from the analyzer which provides an indicator/representation of the probability that the opacity is indicative of a specified underlying cause.

In one arrangement, the region of interest is in the 4 cm×4 cm size. As such, a feature of imaging based on the ROI is that accumulated patient dose (from the x-ray imaging source) will be limited to a relatively smaller anatomical region. The neural network or statistical predictive model can be calibrated accordingly, such as to the CT setup.

Figure 2:
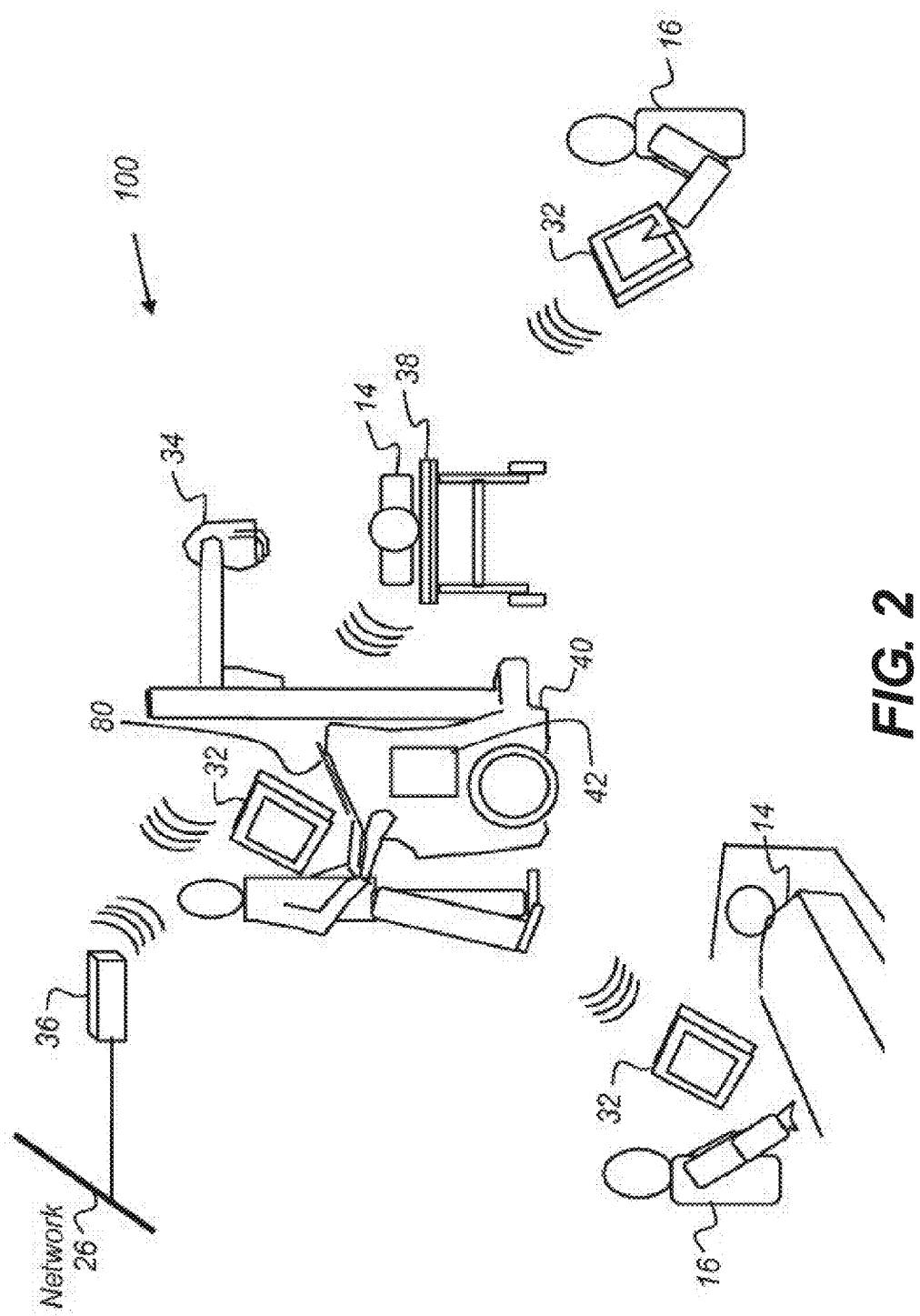
FIG. 2 shows an x-ray imaging system according to an embodiment of the present invention.

FIGS. 1 and 2 illustrated an exemplary digital mobile/portable x-ray imaging system.

The schematic block diagram of FIG. 1 shows a mobile digital radiography system 100 that obtains images of a patient 14 in an ICU or other facility and communicates with a number of medical archiving and radiology databases over a network 26. Among the databases that communicate over network 26 are a Hospital Information System (HIS) 20, a Radiologist Information System 22, and a PACS 24. In addition, one or more optional image processing workstations 30 also receive and process images from mobile digital radiography system 100. Mobile digital radiography system 100 can include a wireless interface 36 to network 26, typically connecting to a wireless hub or similar data communications interface device. Those skilled in the art will recognize that the use of a wireless interface offers an advantage for system usability, flexibility, and information access, as described subsequently.

FIG. 2 shows a schematic block diagram of mobile digital radiography system 100 in one embodiment. A cart 40 having an x-ray source 34 with the x-ray generator and related components for passing x-ray radiation through a portion of the patient's body and on to a digital detector 38. X-ray source 34 includes a collimator or collimating means to collimate the emitted beam of x-ray. A computer 42, shown within cart 40 in this embodiment, provides the control logic for controlling a number of functions, including controlling the x-ray generation from x-ray source 34, obtaining the digital image data from detector 38, and controlling the transfer of data with network 26 and with one or more display interface units 32 that provide an operator interface display. An optional secondary display 80, such as a high-resolution display monitor, is also being provided as part of cart 40.

A detachable display interface units 32 can be used as portable operator consoles of mobile digital radiography system 100 for communication of patient images, patient data and history, instructions, and other data. Display interface unit 32 provides access to mobile digital radiography system 100 in a number of ways. For example, a technologist can use display interface unit 32 as an operator console for obtaining workflow sequence instructions, obtaining information relevant to obtaining a suitable image for each patient, for entering of instructions for controlling the imaging apparatus itself such as for initiating exposure, and for initial quality control (QC) checks of image quality. An attending physician 16 uses display interface 32 to enter instructions and work orders for the image or images needed for a particular patient. The ICU staff use display interface 32 to check the status of imaging requests and to obtain notification that requested images have been obtained. Display interface 32 also serves for interpretation of the patient condition for another physician 16 at the bedside, allowing a comparison with data from prior examinations and allowing interpretation of proper positioning of tubing or other lines, for example.

Figure 3:
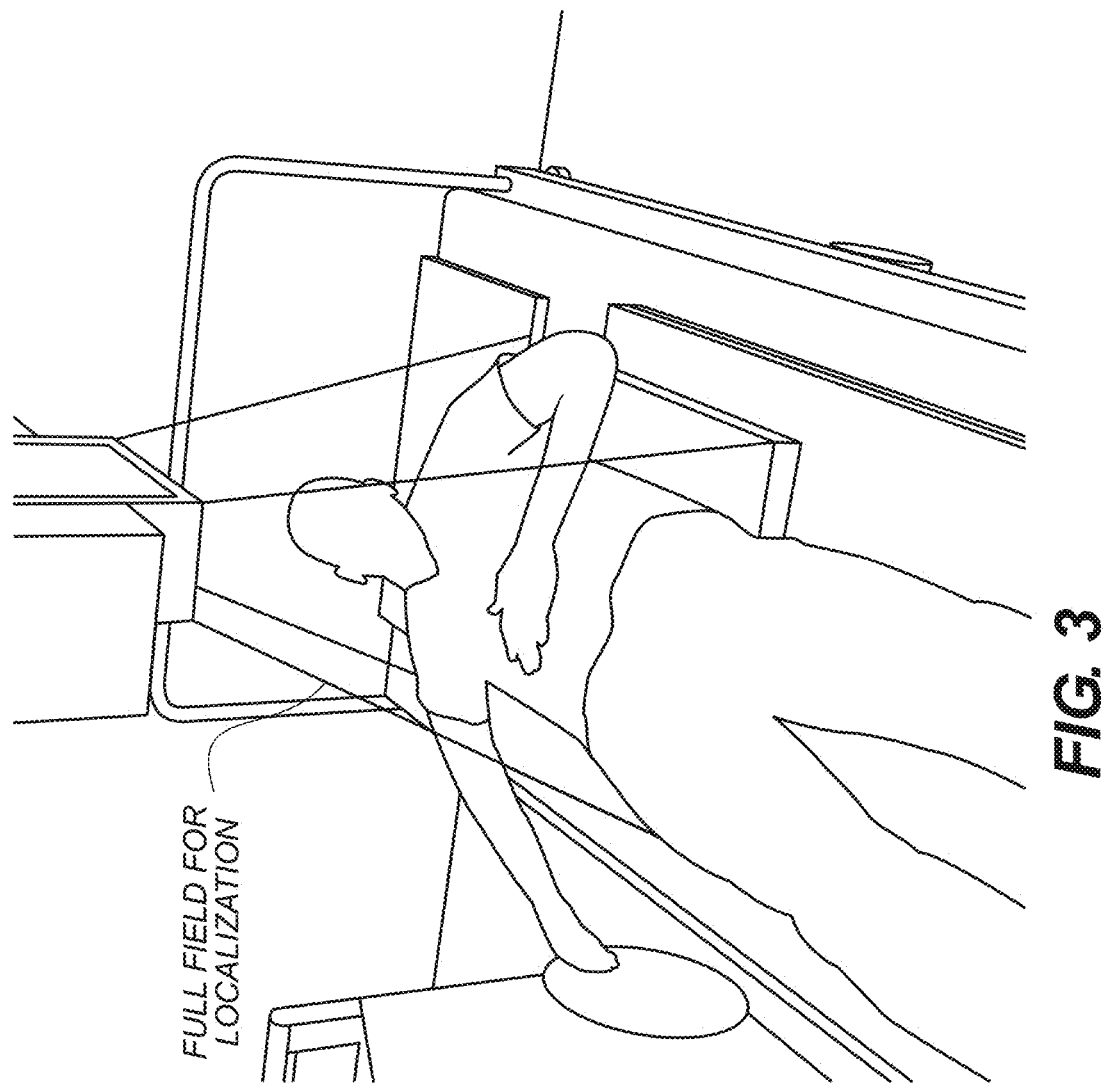
FIG. 3 shows a full field for localization of an x-ray imaging system according to an embodiment of the present invention.

FIG. 3 illustrates an x-ray beam emitted from x-ray source 34 being directed toward patient 14 for capturing of an x-ray image using detector 38. As illustrated, the x-ray beam emitted from x-ray source 34 has not been collimated by a collimator, and thus is show as a full field of localization.

Figure 4:
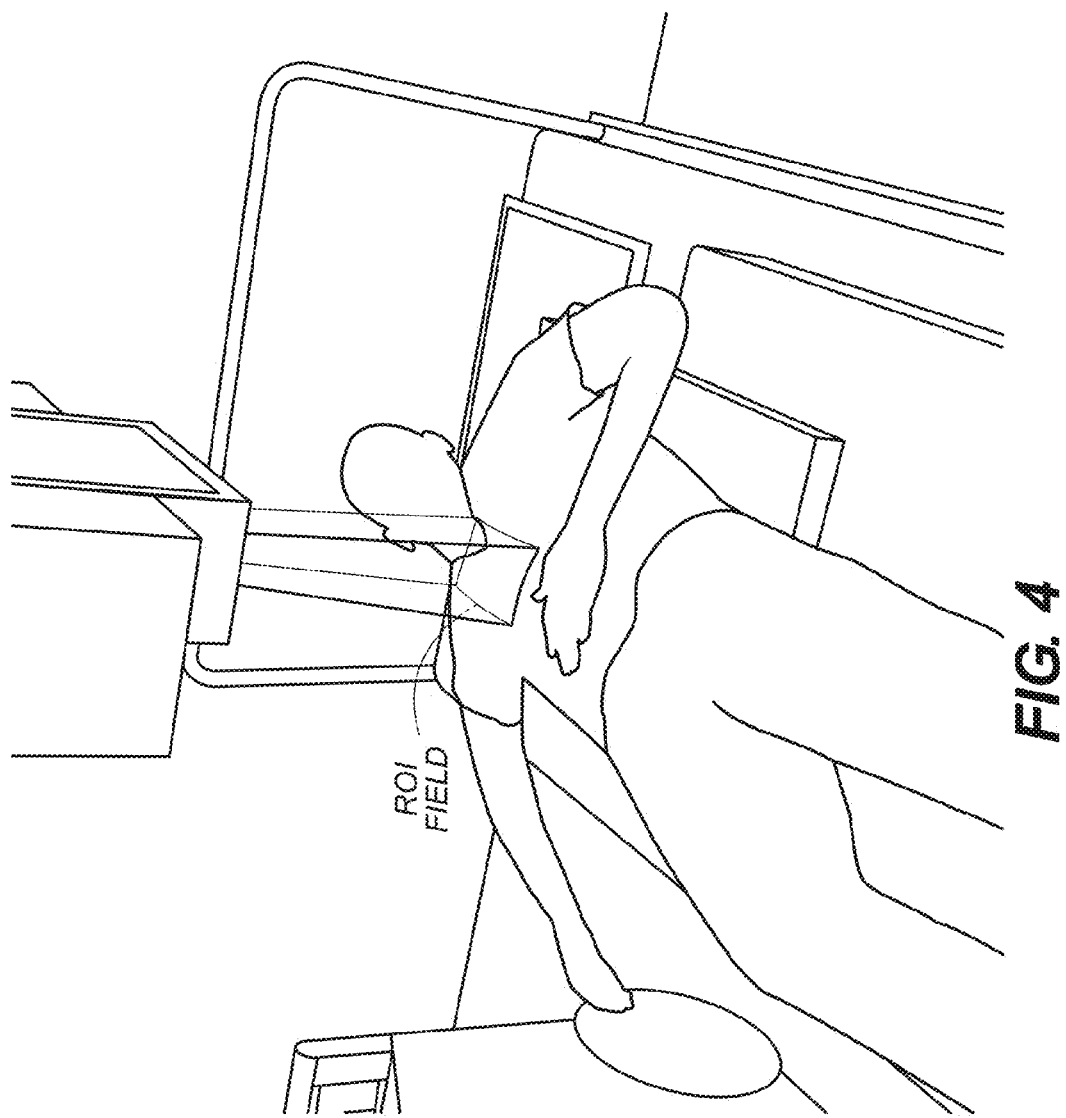
FIG. 4 shows a region of interest field of an x-ray imaging system according to an embodiment of the present invention.

Referring to FIG. 4, the beam of light from x-ray source 34 has been collimated by a collimator, and therefore, the beam of light emitted from x-ray source 34 has been collimated to a region of interest for the capture of an image (i.e., and ROI image) by detector 38.

Collimators are well known to those skilled in the art, for example, as described in U.S. Pat. No. 6,118,842 (Arai), incorporated herein by reference. Collimation can be used during the x-ray exposure to reduce unnecessary radiation to the anatomy that is irrelevant to diagnosis and to confine the x-rays to a local region.

Figure 5B:
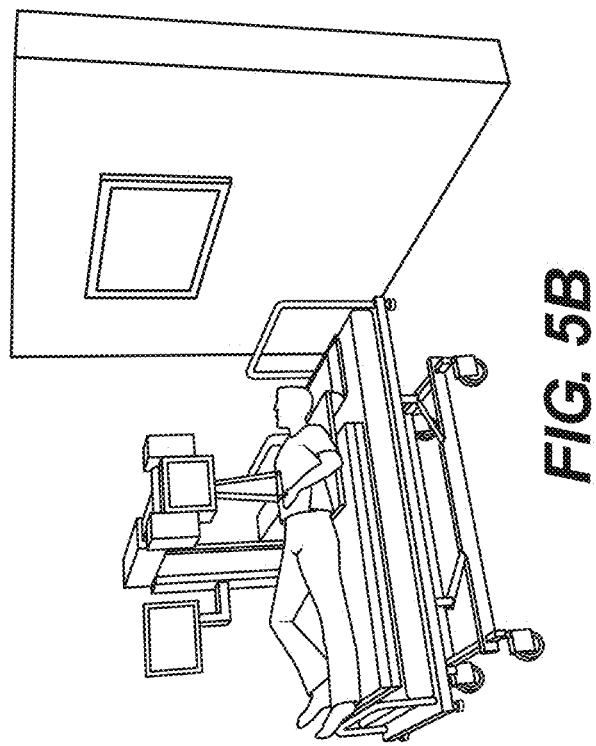
FIGS. 5A and 5B show a wired detector arrangement of an imaging system of FIG. 1.
Figure 5A:
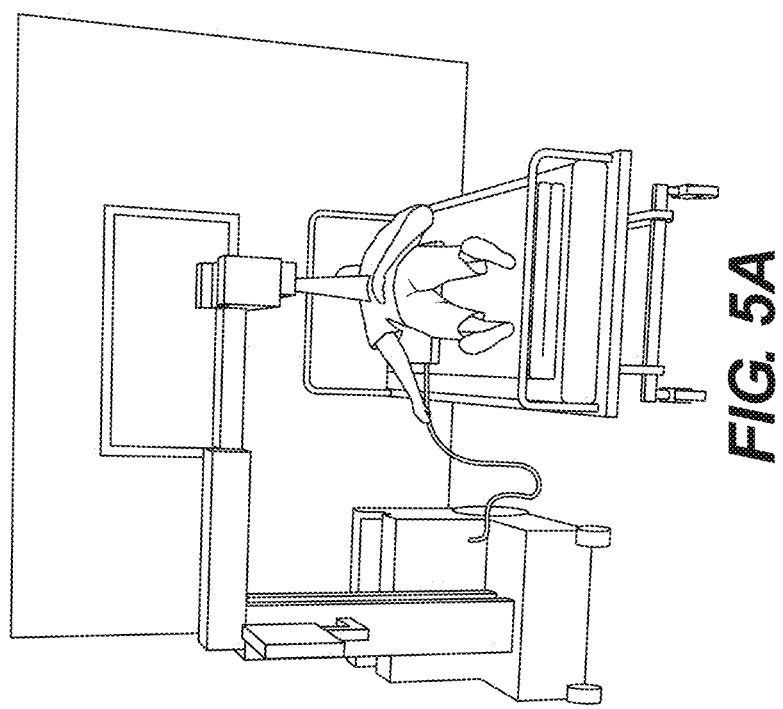

FIGS. 5A and 5B show additional views of the system wherein a wired arrangement is employed. As illustrated, the x-ray beam of light has been collimated.

Figure 6:
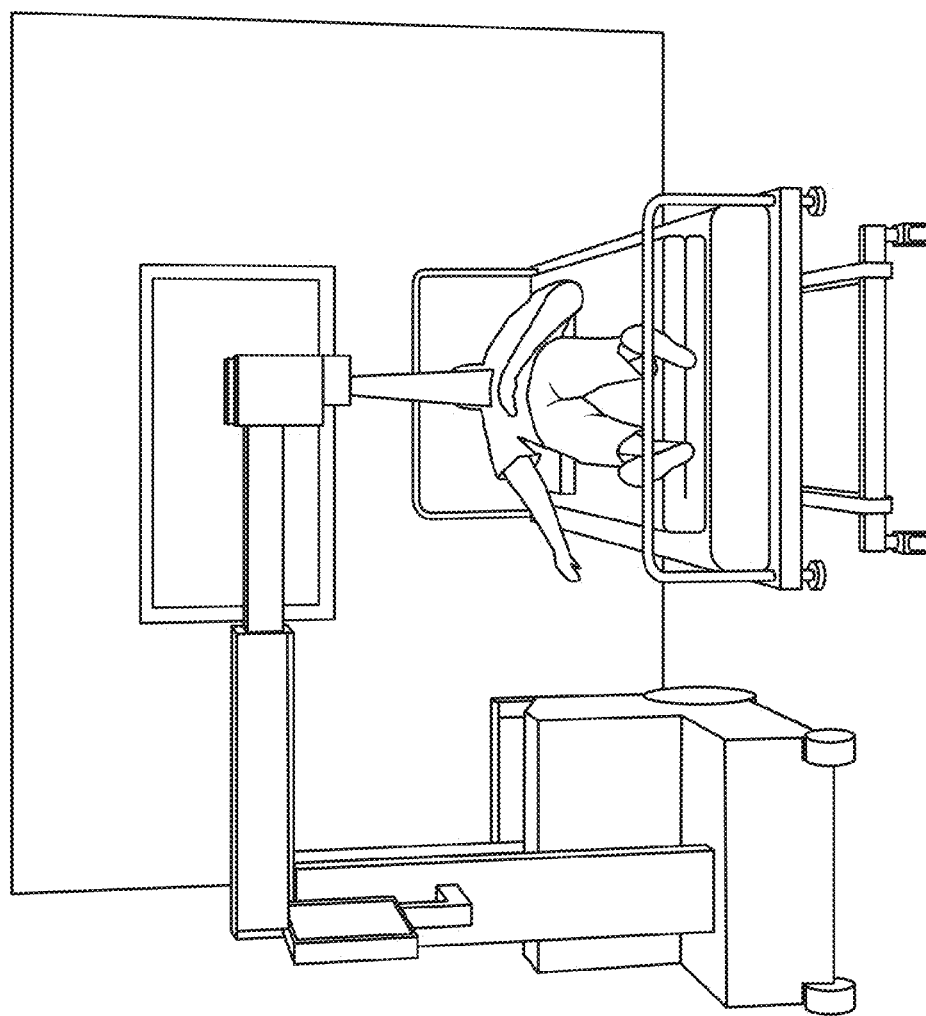
FIG. 6 shows a wireless detector arrangement of an imaging system of FIG. 1.

FIG. 6 shows the system wherein a wireless arrangement is employed. As illustrated, the x-ray beam of light has been collimated.

Figure 7:
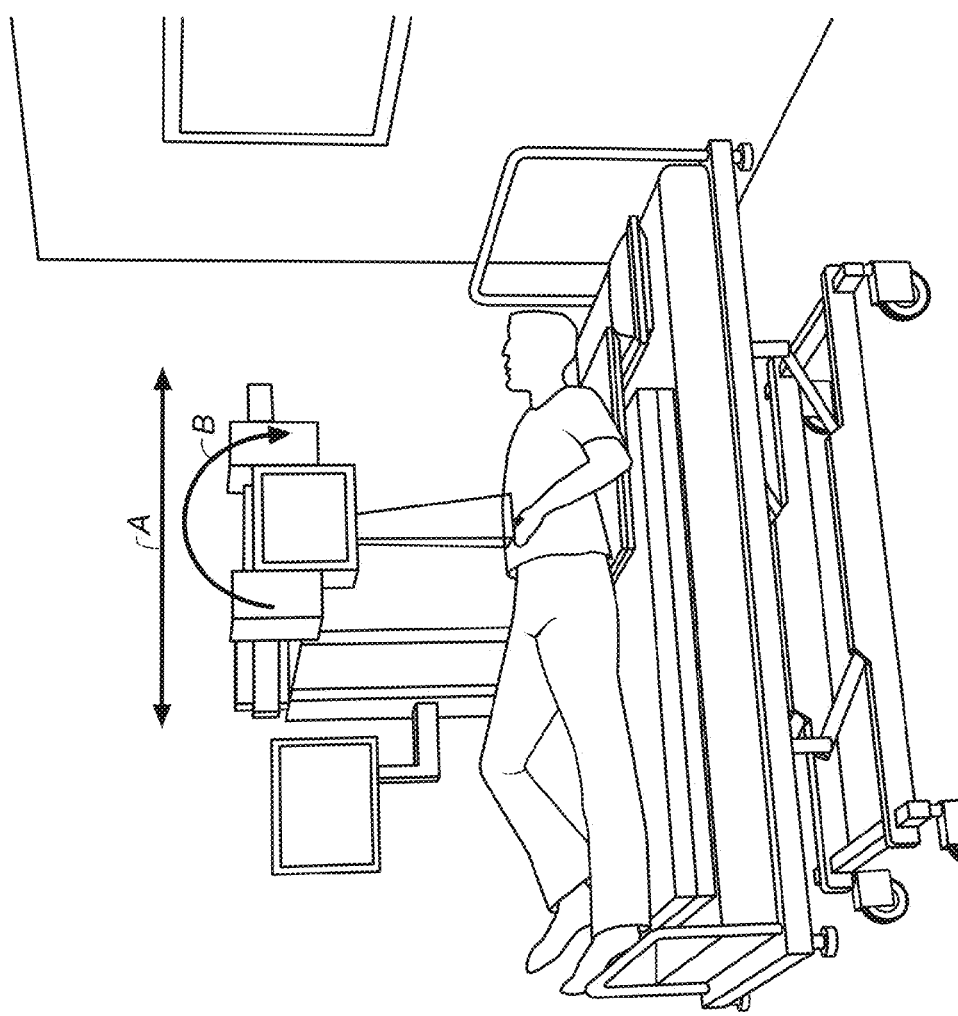
FIG. 7 shows an x-ray imaging system of FIG. 1 having a positioning system for translating and/or rotating an x-ray source.

FIG. 7 illustrates a positioning system to translate (arrow A) and/or rotate (arrow B) collimated light from x-ray source 34 to achieve depth information for the region of interest. By translating and/or rotating x-ray source 34, a plurality of x-ray images—each image focusing the ROI at a different depth of the patient—can be acquired. Accordingly, there is acquired a plurality of x-ray images achieving depth information.

Figure 8:
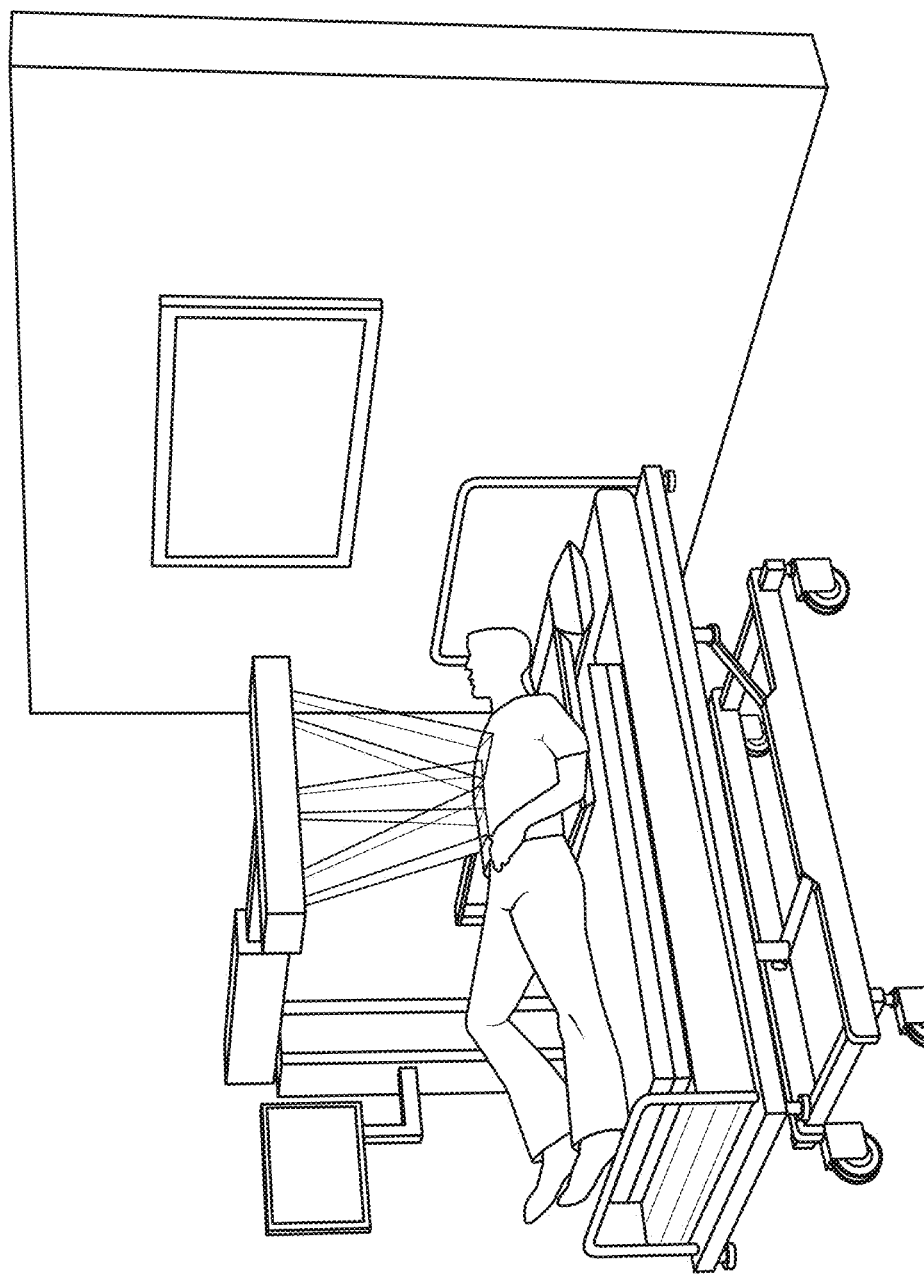
FIG. 8 shows an x-ray imaging system of FIG. 1 having a positioning system having a plurality of x-ray sources.

Similarly, referring to FIG. 8, a stationary positioning system comprised of a plurality of x-ray sources can be employed. In this arrangement, each x-ray source is disposed at a different angle/position relative to the patient, yet each x-ray source can be collimated to an identified region of interest on the patient. With this arrangement, each x-ray image captures an image of the region of interest with a different geometry.

Figure 9:
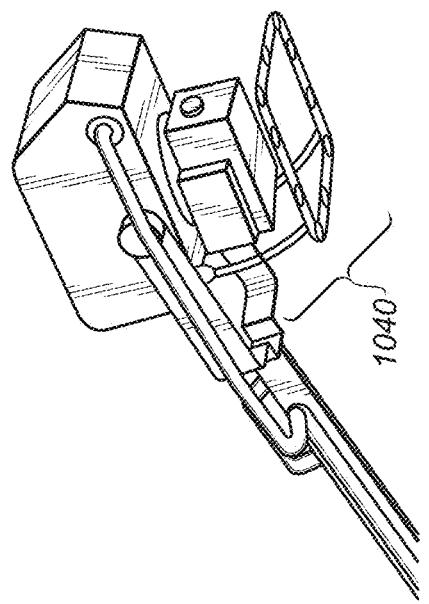
FIGS. 9 and 10 show an exemplary radiographic imaging systems including an x-ray source assembly having first and second (e.g., multiple) radiographic x-ray sources.
Figure 9:
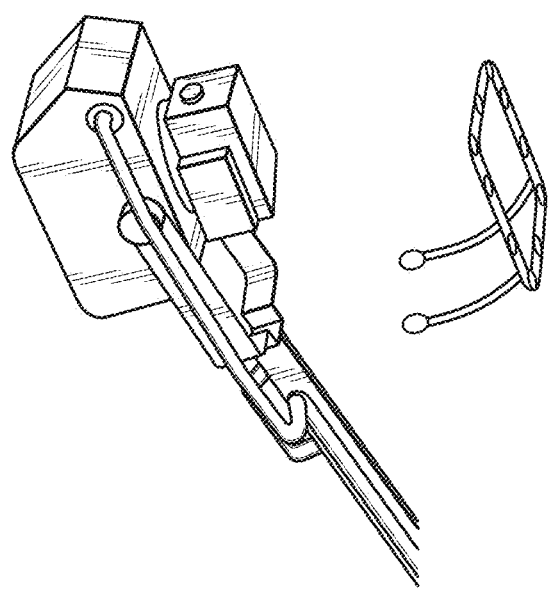
Figure 10:
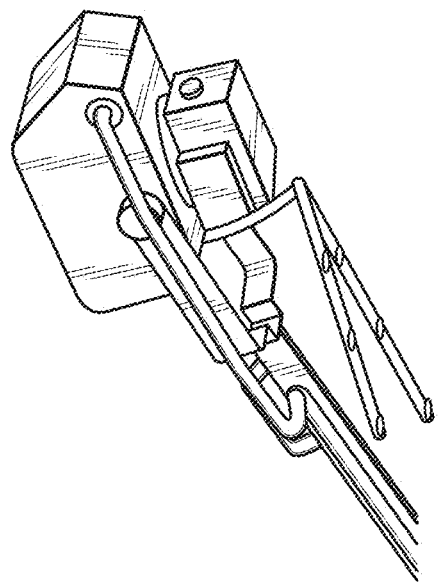
Figure 10:
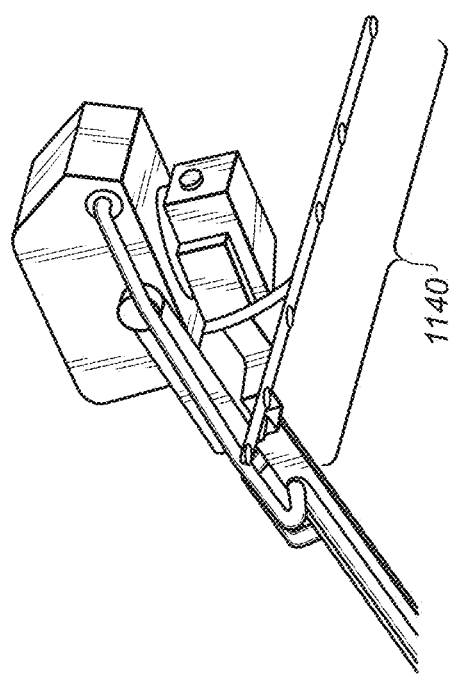

FIGS. 9 and 10 are a diagram that shows exemplary radiographic imaging systems including an x-ray source assembly that can include first and second (e.g., multiple) radiographic x-ray sources. As shown, an x-ray source assembly 1040 of a radiographic imaging system can include a first radiographic x-ray source and collimator, and a second x-ray source comprising a distributed source (e.g., rectangle in FIG. 9 and linear in FIG. 10) that can be individually adjusted (e.g., collimated) and either permanently attached or attached (e.g., detachable) when needed.

Accordingly, there is shown a positioning system that allows images of the identified region of interest to be captured with different geometries, x-ray focus spot sizes, or other acquisition system parametric variations that can produce images of the ROI having different characteristic properties.

Figure 11:
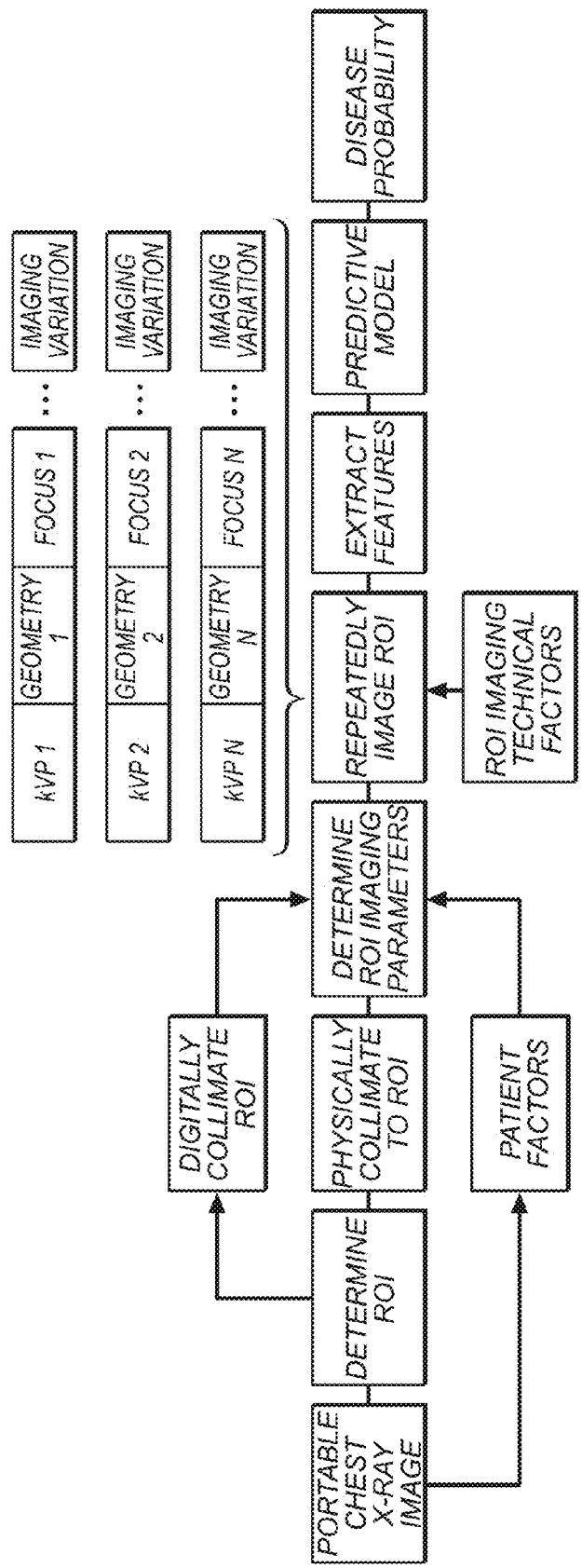
FIG. 11 generally illustrated a method according to the present invention.

The method is generally illustrated in the flow diagram shown in FIG. 11. As illustrated, using an x-ray imaging system, a first x-ray image of a chest I-1 is captured and a region of interest ROI-1 is identified within the first image I-1. The x-ray imaging system is then configured to capture another x-ray image I-2 of the same region of interest using a different acquisition system parameter. For example, by translating/rotating/moving the x-ray source (such as shown in FIG. 7) or using a different x-ray source (such as shown in FIG. 8) so as to capture an image of the identified region of interest using different geometries, x-ray focus spot sizes, or other acquisition system parametric variations to produce an image of the ROI having different characteristic properties.

This is repeated wherein a plurality of images are acquired, each image including the same/identified region of interest, but captured using a different acquisition system parameter.

Still referring to FIG. 11, a processing engine is employed to extract features from each of the ROI of the images. The extracted features are then analyzed using an analyzer such as a statistical predictive model or trained neural network. Such processing engines, statistical predictive models, and trained neural networks are known to those skilled in the art. Training is performed using prior images from different patients acquired on portable imaging systems and other modalities such as CT where the ground truth is known. Features such a texture, opacity, pixel value, and the like, are extracted to provide biomarkers (i.e., quantitative features) and correlated with different diseases. The information provided by the features is improved by the increased amount/number of ROI images acquired under different imaging conditions. Features that provide the best/optimum predictive models for various diseases are identified and yield an index for each diseases which correlates with the probability of each disease being present.

A disease probability output is generated which provides an indicator/representation/index of the probability of the disease. For example, that the opacity is indicative of a specified underlying cause. This output can be displayed on display 32 or other visual device. Those skilled in the art will recognize that the output can be numerical, index, iconic, graphical, color coded, in the form of a chart or illustration, or the like.

Figure 12:
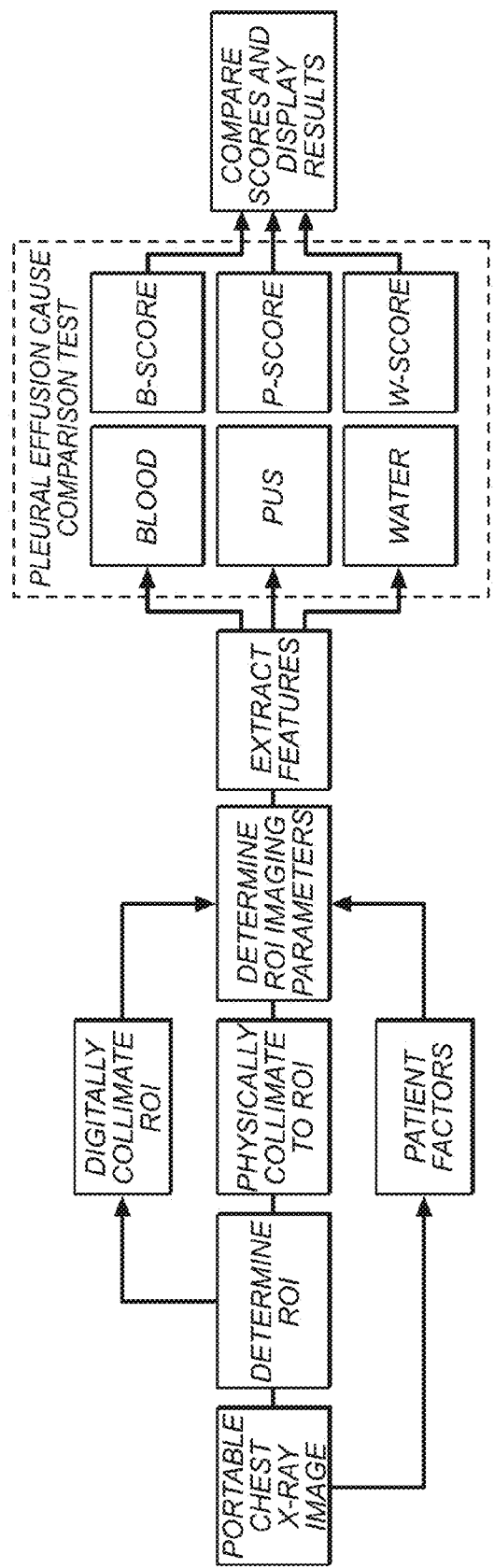
FIG. 12 shows a method for one embodiment according to the present invention.

FIG. 12 provides an example wherein features are extracted to evaluate pleural effusion causes, such as blood, pus, and water. A pleural effusion cause comparison test is accomplished, scores are compared, and results are displayed.

Figure 13A:
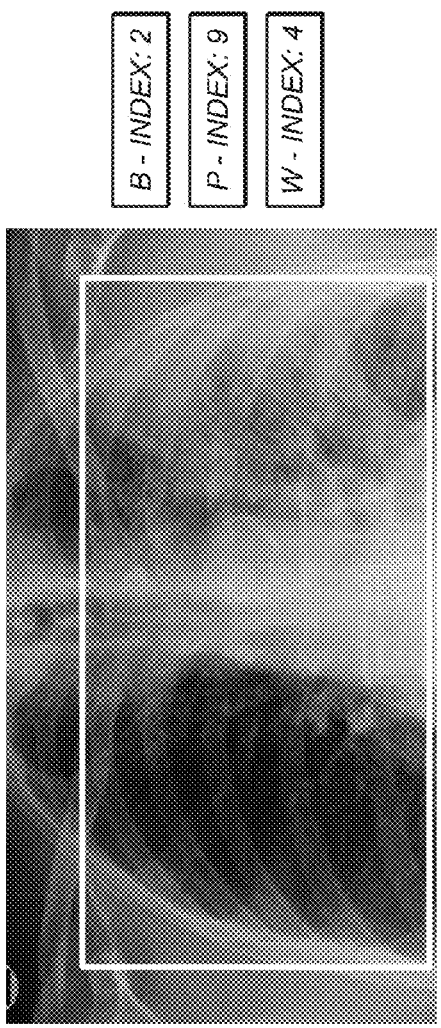
FIGS. 13A and 13B illustrate examples of an output.
Figure 13B:
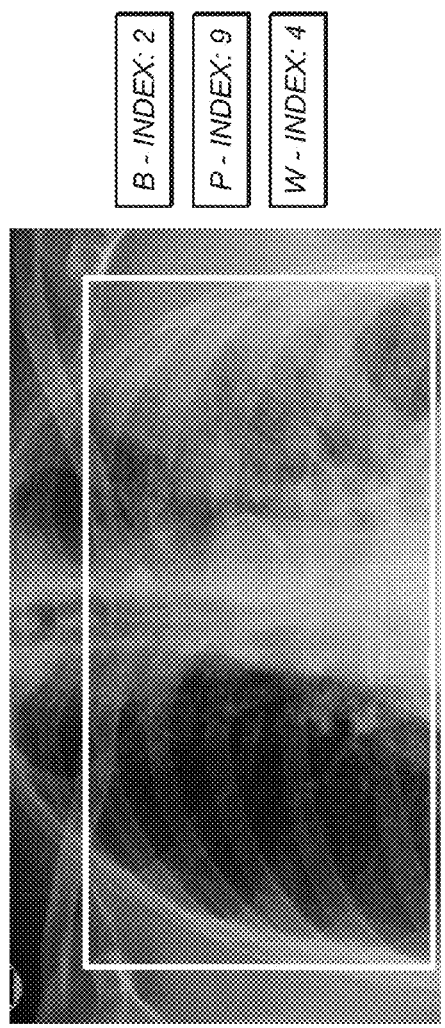

FIGS. 13A and 13B show examples of a display output which compares scores and displays results. The features are extracted and the probability for each cause is computed from which an index is generated and provides a relative score that indicates to the user which possible cause of the pleural effusion is most likely based on the extracted information.

It is noted that the method is not limited to conventional digital portable X-ray imaging systems, but can also be employed by non-portable systems.

In at least one arrangement, the method employ images of the ROI from other/multiple modalities, including but not limited to, ultrasound, photon counting systems with energy discriminating capability, photo-acoustic imaging, and limited angle tomosynthesis.

In some arrangements, it may be desired to employ contrast media.

In some arrangements, it may also be desired to employ image processing techniques such as rib suppression since it may be achieve greater performance.

Applicants recognize that other approaches for imaging the ROI include multi-frame averaging to achieve a high signal-to-noise ratio (SNR).

The system may be used for real time x-ray imaging (e.g., fluoroscopy for the ROI) and real time tomosynthesis imaging of the ROI, which may have benefits for imaging in the operating room, or for supporting bedside interventional procedures such as tube and line placements.

In the following description, a preferred embodiment of the present invention will be described as a software program. Those skilled in the art will recognize that the equivalent of such software may also be constructed in hardware. Because image manipulation algorithms and systems are well known, the present description will be directed in particular to algorithms and systems forming part of, or cooperating more directly with, the method in accordance with the present invention. Other aspects of such algorithms and systems, and hardware and/or software for producing and otherwise processing the image signals involved therewith, not specifically shown or described herein may be selected from such systems, algorithms, components and elements known in the art.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The methods described above may be described with reference to a flowchart. Describing the methods by reference to a flowchart enables one skilled in the art to develop such programs, firmware, or hardware, including such instructions to carry out the methods on suitable computers, executing the instructions from computer-readable media. Similarly, the methods performed by the service computer programs, firmware, or hardware are also composed of computer-executable instructions.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim.

In the following claims, the terms "first," "second," and "third," and the like, are used merely as labels, and are not intended to impose numerical requirements on their objects.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A flat panel digital radiography imaging system, comprising:
    an x-ray source adapted to emit an x-ray beam onto an identified region of interest;
    a positioning system to translate or rotate the x-ray source from a first position to a second position, wherein the second position is different than the first position;
    a digital x-ray detector adapted to capture a first 2D projection image of the region of interest when the x-ray source is in the first position, and capture a second 2D projection image of the region of interest when the x-ray source is in the second position;
    a processing engine to extract at least one feature from each of the region of interest of the first and second captured 2D projection images, wherein the at least one extracted feature evaluates at least one of the following: lung nodule, lung cancer, pneumothorax, thickened lung tissue, pneumonia, and pulmonary tuberculosis; and
    an analyzer analyzing the extracted features and generating an indicator of a disease responsive to the extracted features.

2. The system of claim 1 wherein the identified region of interest of each captured image are captured with different geometries, x-ray focus spot sizes, or other acquisition system parametric variations that can produce images of the region of interest having different characteristic properties.

3. The system of claim 1 wherein the extracted features include texture, opacity, and pixel value.

4. The system of claim 1 further comprising a collimator to collimate the x-ray beam to the identified region of interest.

5. A flat panel digital radiography imaging system, comprising:
    an x-ray source adapted to emit an x-ray beam onto an identified region of interest;
    a first x-ray source disposed in a first position;
    a second x-ray source disposed in a second position, wherein the second position is different than the first position;
    a digital x-ray detector adapted to capture a first 2D projection image of the region of interest using the first x-ray source disposed in the first position, and capture a second 2D projection image of the region of interest using the second x-ray source disposed in the second position;
    a processing engine to extract at least one feature from each of the region of interest of the first and second captured 2D projection images, wherein the extracted feature evaluates at least one of the following: lung nodule, lung cancer, pneumothorax, thickened lung tissue, pneumonia, and pulmonary tuberculosis; and
    an analyzer analyzing the extracted features and generating an indicator of a disease responsive to the extracted features.

6. The system of claim 5 wherein the identified region of interest of each captured image are captured with different geometries, x-ray focus spot sizes, or other acquisition system parametric variations that can produce images of the region of interest having different characteristic properties.

7. The system of claim 5 wherein the extracted features include texture, opacity, and pixel value.

8. The system of claim 5 further comprising a collimator to collimate the x-ray beam to the identified region of interest.

9. The system of claim 5 further comprising a display for displaying the indicator.

10. A method for flat panel digital radiography imaging, comprising:
- emitting a first x-ray beam from an x-ray source disposed in a first position;
- directing the first x-ray beam onto an identified region of interest (ROI) and capturing a first ROI projection image;
- emitting a second x-ray beam from the x-ray source disposed in a second position, wherein the second position is different than the first position;
- directing the second x-ray beam onto the identified region of interest and capturing a second ROI 2D projection image;
- processing the first and second ROI 2D projection images to extract at least one feature from each of the first and second ROI 2D projection images;
- analyzing the at least one extracted feature to evaluate at least one of the following: lung nodule, lung cancer, pneumothorax, thickened lung tissue, pneumonia, and pulmonary tuberculosis;
- generating at least one indicator of a disease responsive to the analyzed at least one extracted feature; and
- storing, displaying, or transmitting the at least one indicator.

11. The method of claim 10 wherein the first and second x-ray beams are emitted from the same x-ray source.

12. The method of claim 10 wherein the first and second x-ray beams are emitted from different x-ray sources.

13. The method of claim 10 wherein the identified region of interest of each captured ROI projection image are captured with different geometries, x-ray focus spot sizes, or other acquisition system parametric variations that can produce images of the region of interest having different characteristic properties.

14. The method of claim 10 wherein the extracted features include texture, opacity, and pixel value.

* * * * *